United States Patent [19]

Takemoto et al.

[11] 4,144,646
[45] Mar. 20, 1979

[54] TORSIONAL ULTRASONIC VIBRATORS

[75] Inventors: Kiyochika Takemoto, Kodaira; Yasuo Suzuki, Kurume; Yoshihito Ochiai, Fujisawa; Syozi Nakashima, Yamanishi; Midori Hayashi, Yamakita, all of Japan

[73] Assignees: Lion Hamigaki Kabushiki Kaisha; Kano Denki Kabushiki Kaisha, both of Japan

[21] Appl. No.: 746,818

[22] Filed: Dec. 2, 1976

Related U.S. Application Data

[63] Continuation-in-part of Ser. No. 743,157, Nov. 18, 1976.

[30] Foreign Application Priority Data

Dec. 5, 1975 [JP] Japan .................. 50-145273

[51] Int. Cl.² ............................ A61C 3/00
[52] U.S. Cl. ..................... 32/40 R; 128/24 A; 32/DIG. 4; 128/172.1
[58] Field of Search ............. 128/172.1, 24 A, 62 A, 128/409, 136; 32/40 R, 58, 59, DIG. 4

[56] References Cited

U.S. PATENT DOCUMENTS

| | | | |
|---|---|---|---|
| 1,818,146 | 8/1931 | Maker | 128/136 X |
| 2,990,616 | 7/1961 | Balamuth et al. | 32/DIG. 4 |
| 3,058,218 | 10/1962 | Kleesattel | 128/24 A X |
| 3,526,219 | 9/1970 | Balamuth | 32/58 X |

FOREIGN PATENT DOCUMENTS 1954272  5/1970  Fed. Rep. of Germany ...... 32/DIG. 4

OTHER PUBLICATIONS

*The Improved Carborundum Dental Goods*, 1937.

*Primary Examiner*—Lee S. Cohen
*Attorney, Agent, or Firm*—Steinberg & Blake

[57] ABSTRACT

A torsional ultrasonic vibrator particularly adapted for treating teeth by exposing them to ultrasonic waves in the presence of a tooth-decay retarding agent which engages the teeth. A shaft which has a central axis has fixed thereto a blade which projects from the latter axis while having a size small enough to be situated in the mouth of an individual to be treated and large enough to extend along a plurality of teeth in the mouth. A vibrator is operatively connected with this shaft for angularly oscillating the same about the above axis at an ultrasonic frequency.

11 Claims, 18 Drawing Figures

FIG. 4A
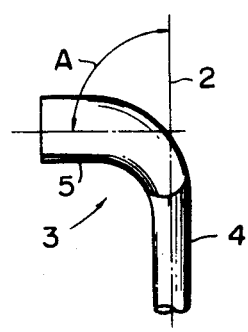
FIG. 5A
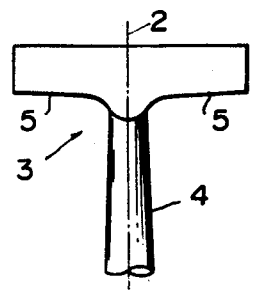
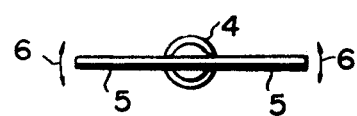
FIG. 4B
FIG. 5B
FIG. 6A
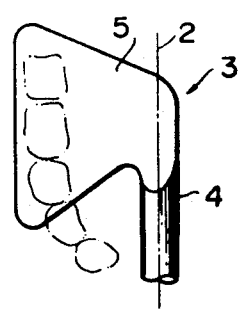
FIG. 7A
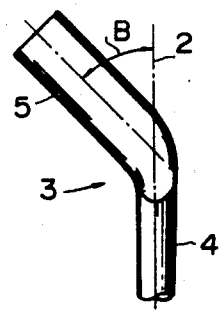
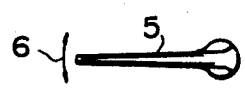
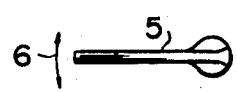
FIG. 6B
FIG. 7B

TORSIONAL ULTRASONIC VIBRATORS

CROSS REFERENCE TO RELATED APPLICATION

This application is a continuation-in-part of copending application Ser. No. 743,157, filed Nov. 18, 1976.

BACKGROUND OF THE INVENTION

The present invention relates to apparatus for treating teeth.

In particular, the present invention relates to an apparatus for forming on the surface of the teeth a reinforcing layer of a tooth-decay retarding agent by exposing the surface of the teeth to ultrasonic radiation while the teeth are contacted by the tooth-retarding agent.

It is well known that in order to prevent tooth decay the surface of the teeth can be coated with a tooth-decay retarding agent such as tin fluoride, sodium fluoride, or fluoroamine. However, in the event that the entire treatment consists only in coating the teeth with such an agent, this coating does not adhere strongly to the teeth and within a relatively short time is dissolved away. Thus, it is impossible with such a treatment to achieve a long-lasting decay-retarding effect. Furthermore, even while the coating of the tooth-decay retarding agent is at the surface of the teeth, there is still an insufficient extent of prevention of dissolving of calcium from the surface of the teeth.

Recently it has been proposed to provide a method according to which the teeth are exposed to ultrasonic waves while in contact with a tooth-decay retarding agent, so as to form in this way a reinforcing protective layer of the decay-retarding agent on the teeth at the surface thereof. While this effect was discovered, nevertheless an apparatus suitable for providing the treatment was not available.

A known ultrasonic cutter was used for the ultrasonic vibrator. However, since this cutter is designed to perform a cutting operation only on a limited localized area, when used for carrying out the above treatment so as to form a reinforcing layer of tooth-decay retarding agent over a relatively large tooth surface, the operating efficiency was extremely low. It was therefore found that such an ultrasonic cutter was of no practical value in connection with a tooth treatment of the above type.

Furthermore, since the known vibrators of the above type provide vertical vibrations, difficulty was encountered in applying the ultrasonic waves directly to the ends of the teeth, and in addition it was found to be practically impossible to apply the ultrasonic waves to the rear or inner, back surfaces of the teeth. Furthermore, it has been found preferable to provide for a treatment of the above type a relatively low ultrasonic frequency, and for this purpose when using a known ultrasonic cutter of the above type, the size of the latter had to be enlarged considerably in order to achieve the relatively low ultrasonic vibrating frequency. This factor resulted in an increase in the size of the apparatus to such an extent that it could not be properly situated in the oral cavity. Thus, an effective treatment utilizing ultrasonic waves of relatively low frequency could not be achieved by using a known apparatus such as an ultrasonic cutter as referred to above.

SUMMARY OF THE INVENTION

It is accordingly a primary object of the present invention to provide an apparatus for carrying out a treatment as set forth above while solving the problems referred to above.

In particular, it is an object of the present invention to provide a torsional ultrasonic vibrator which can conveniently be utilized for the purpose of exposing teeth to ultrasonic vibrations while in the presence of a tooth-decay retarding agent.

In particular, it is an object of the present invention to provide an apparatus of the above type which can simultaneously expose teeth at their ends as well as at their front and back surfaces to the ultrasonic radiation.

In addition, it is an object of the present invention to provide an apparatus of this type which can simultaneously treat a plurality of teeth, even all of the teeth at one time, if desired.

Furthermore, it is an object of the present invention to provide an apparatus of the above type which is relatively simple and reliable in operation as well as convenient to operate.

According to the invention the tooth-treating apparatus includes a shaft which has a central axis and a blade which is fixed to the shaft and which extends at least in part to one side of the latter axis. A vibrator means is operatively connected with this shaft for angularly oscillating the same about the above axis at an ultrasonic frequency. The size of the blade is such that it can conveniently be situated in the mouth of an individual extending along a plurality of teeth so that in this way, while the teeth are contacted by a tooth-decay retarding agent, the teeth can be exposed to the ultrasonic waves.

BRIEF DESCRIPTION OF DRAWINGS

The invention is illustrated by way of example in the accompanying drawings which form part of this application and in which:

FIGS. 4A and 4B are respectively elevation and top plan views of one embodiment of a shaft and blade of the invention;

FIGS. 5A and 5B are respectively elevation and top plan views of a second embodiment of a shaft and blade of the invention;

FIGS. 6A and 6B are elevation and top plan views of a further embodiment of a shaft and blade of the invention;

FIGS. 7A and 7B are elevation and top plan views of a further embodiment of a shaft and blade of the invention;

DESCRIPTION OF PREFERRED EMBODIMENTS

Figure 1:
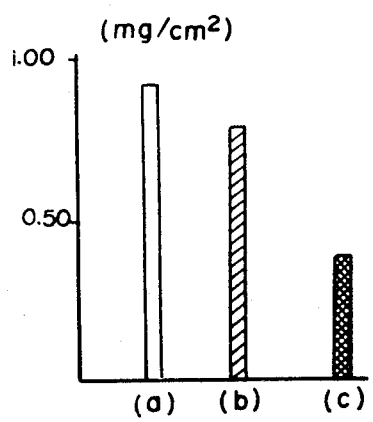
FIGS. 1 and 2 are graphs illustrating the effects which are achieved by way of the present invention.
Figure 2:
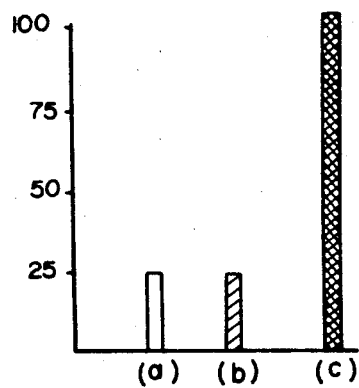

As has been referred to above, it has been found that highly superior results can be achieved by exposing teeth to ultrasonic radiation while the teeth are in contact with a tooth-decay retarding agent. These effects are illustrated in FIGS. 1 and 2. FIG. 1 is a graph illustrating the amount of $Ca^{++}$ ions dissolved out when treating different tooth samples. Thus FIG. 1 illustrates these effects in connection with three samples (a), (b), and (c). Sample (a) is a portion of an untreated human tooth, while sample (b) is a portion of a human tooth which was dipped in an 8% $SnF_2$ solution for five minutes, and sample (c) is a portion of a human tooth which was exposed to radiation in the form of ultrasonic vibrations at a frequency of 19 KHz while this sample was dipped in an 8% $SnF_2$ solution for three minutes. All of the above samples, namely the untreated sample (a), the sample (b) which was only contacted by the above solution for five minutes, and the sample (c) which in addition to being contacted by the above solution for three minutes was exposed to the above ultrasonic radiation, were dipped in a buffer solution containing 0.1 mole/l of acetic acid at 37° C. for five hours. Thus, while the extent of calcium dissolved out with sample (b) was somewhat less than that of the untreated tooth, it will be seen that a substantially smaller amount of calcium was dissolved out of sample (c), thus demonstrating the superior results achieved by exposing the tooth to the ultrasonic radiation while in the presence of the tooth-decay retarding agent.

FIG. 2 is a graph illustrating the Vickers hardness of the above samples after they were dipped in the above buffer solution of acetic acid for five hours to effect deliming. Thus it will be seen from FIG. 2 that while there was no difference in the Vickers hardness between the samples (a) and (b), the Vickers hardness of sample (c) was outstandingly superior to the other samples.

Figure 3:
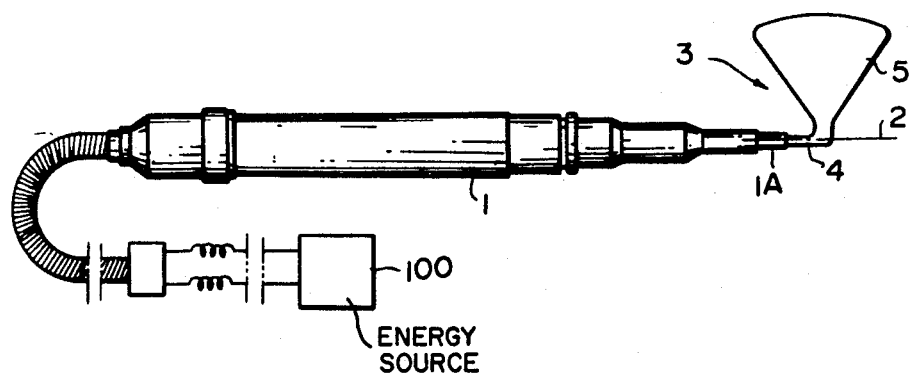
FIG. 3 is a schematic elevation of one possible apparatus of the invention.

Referring now to FIG. 3, the structure of the invention which is illustrated therein includes a shaft 4 which has a central shaft axis 2. Operatively connected with the shaft 4 is a vibrator means 1 which angularly oscillates the shaft 4 around the axis 2 thereof. It will be seen that the vibrator means 1 is elongated and extends along the axis 2, this vibrator means having its portion 1A connected in any suitable way to the shaft 4. For example the portion 1A may be in the form of a sleeve receiving a part of the shaft 4 and suitably keyed thereto so that the shaft 4 oscillates with the portion 1A of the torsional vibrator 1 which is of a known construction. Energy is supplied to the vibrator 1 from the source 100.

Operatively connected with the shaft 4 so as to oscillate therewith is a vibratory member 3 in the form of a blade 5 which in the illustrated example is of a substantially triangular configuration and extends laterally to one side only of the axis 2, being situated in a plane which contains the shaft axis. This blade 5 has a narrow portion adjacent to and, for example, formed integrally with the shaft 4 at an end thereof distant from the vibrator means 1, and the blade 5 becomes gradually wider, in the direction of the axis 2, toward the outer edge region of the blade 5 which is distant from the axis 2. Thus, the relatively thin blade 5 extends in a plane containing the axis 2, and a relatively small amplitude of oscillatory ultrasonic vibration is transmitted to the blade 5 so that the latter oscillates around the axis 2 in order to radiate ultrasonic waves. Depending upon the length of the blade 5, variations of which are illustrated in FIGS. 4, 5, 9, and 10, deflectional vibrations will be generated at the blade 5 and ultrasonic waves will be emitted from the surface thereof, in directions perpendicular to the opposed surfaces of the blade 5. Thus, with the structure of the invention the known torsional vibrator means 1 is utilized so that a detailed description thereof is omitted. The source 100 provides suitable oscillatory energy for operating the vibrator means 1.

In the embodiment of FIGS. 4A and 4B, it will be seen that the vibratory member 3 includes the blade 5 which also extends laterally from the axis 2 of the shaft 4, being fixed to and integral with the latter, this blade 5 in this case also making an angle A of 90° with respect to the axis 2, as illustrated in FIG. 4A. As is apparent from FIG. 4B, the thickness of the blade 5 is less than the diameter of the shaft 4. When the unit 3 which includes the shaft 4 and the blade 5 is fixed to the terminal portion 1A of the vibrator means 1, the unit 3 will be torsionally vibrated about the axis 2, as indicated by the arrow 6 in FIG. 4B. Thus, the blade 5 will be provided with small-amplitude oscillatory vibrations at ultrasonic frequency, so that ultrasonic waves will be radiated perpendicularly from the opposed faces of the blade 5. The amplitude of the vibrations gradually increases from the axis 2 toward the outer tip or edge region of the blade 5, which is most distant from the axis 2, but effective radiation with ultrasonic waves can be carried out in a relatively broad range in accordance with the area of the blade 5. This area is such that it can comfortably be situated in the mouth of an individual with the blade 5 extending along a plurality of teeth so as to simultaneously treat the latter.

By extending the blade 5 laterally away from the axis 2, it is not only possible to impact ultrasonic vibrations to the blade 5, but in addition there is the advantage of being capable of situating the blade 5 in the immediate vicinity not only of the front of teeth which are to be treated but also in the immediate vicinity of the end and back surfaces of the teeth to be treated, so that the treatment can be greatly facilitated by holding the blade 5 at a particular angle when inserted into the mouth, and of course the elongated vibrator means 1 forms a convenient handle to be held in any desired attitude by the operator, with this attitude of course being easily changed to transmit the ultrasonic waves to desired teeth in order to treat the latter. Thus all the surfaces of the teeth can conveniently be treated very easily in a relatively short time. Moreover, if the blade 5 is held in a substantially horizontal attitude between the upper and lower teeth, then the lower ends of the upper teeth and the upper ends of the lower teeth can be simultaneously treated. Thus the efficiency of the operation can be greatly enhanced and treatment of a large number of teeth can be brought about in a short time.

The embodiment of the invention which is illustrated in FIGS. 5A and 5B includes the unit 3 which has the oscillatory shaft 4 as well as the blade 5 fixed to and projecting laterally therefrom as illustrated, this blade 5 being integral with the shaft 4. In this case it will be seen that the blade 5 extends in opposite directions to both sides of the axis 2 while being perpendicular with respect thereto, and as is apparent from FIG. 5B, the blade 5 is of course thinner than the diameter of the shaft 4. This particular configuration of FIGS. 5A and 5B provides the advantage of enabling the front teeth to be treated in a highly effective manner.

In FIGS. 6A and 6B, there is a further embodiment of the unit 3 according to which the blade 5 thereof has a width, in the direction of the axis 2, which not only gradually increases toward the outer edge region of the blade 5, as was the case with FIG. 3, but which in addition is sufficiently large to extend along a number of teeth indicated in phantom lines in FIG. 6A. As is apparent from FIG. 6A, these teeth are the rear molar or grinding teeth, so that this embodiment is particularly suitable for treating such teeth. Thus the unit 3 of FIGS. 6A and 6B can be inserted from the front of the mouth and a plurality of grinding or molar teeth can be simultaneously treated in a highly effective manner.

Moreover, as is apparent from FIG. 6B, the blade 5 has a thickness which gradually diminishes toward the outer edge region of the blade which is most distant from the shaft 4. In this way the distribution of the mass and a rigidity suitable for generation of ultrasonic waves in a range of a relatively low frequency can be achieved, this frequency being, for example, either 19 KHz or 28 KHz. Thus by properly choosing the mass distribution and rigidity of a particular blade 5, such as those of the above embodiments or those described below, as well as that of FIGS. 6A and 6B, it is possible to provide the desired range of ultrasonic frequency.

In the embodiment of the invention which is illustrated in FIGS. 7A and 7B, the unit 3 includes in addition to the shaft 4 the blade 5 which projects angularly from the axis 2 but at an angle substantially less than 90°. In this case the angle B formed between the blade 5 and the axis 2 is approximately 45°. With this embodiment it is very easy to place the blade 5 in close proximity to particular teeth. The angle B can be optionally chosen and different vibratory units 3 can be designed and used depending upon different sizes of the oral cavities and shapes of the tooth rows and the gingiva. It will be understood of course that the same vibratory unit 1 can be used with different units 3 the shafts 4 of which can be slipped into the sleeve 1A and releasably connected thereto by a suitable key, set screw, or the like.

Figure 8A:
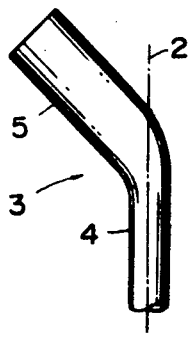
FIGS. 8A and 8B are elevation and top plan views of a still further embodiment of a shaft and blade of the invention.
Figure 8B:
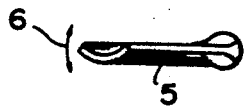
Figure 8C:
FIG. 8C is an illustration of the end of the blade of FIGS. 8A and 8B when looking downwardly toward the blade of FIG. 8A from the upper left region of FIG. 8A.

With the embodiment of the invention which is illustrated in FIGS. 8A, 8B, and 8C, the unit 3 is the same as that of FIGS. 7A and 7B, for example, except that the blade 5 is not flat. In this case the blade 5 has the configuration of an elongated channel, having an inner concave surface and an outer convex surface, as is particularly apparent from FIGS. 8B and 8C. As is apparent from FIG. 8C, the ultrasonic waves which radiate from the concave surface are directed as shown by the arrows 7, so that these waves can become concentrated substantially at a single point, if desired. Accordingly this particular embodiment is highly effective for subjecting a relatively small surface region of the teeth to radiation in the form of relatively strong ultrasonic waves.

Figure 9:
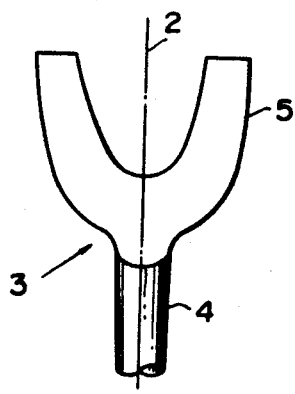
FIG. 9 is an elevation of an embodiment of a shaft and blade where the latter can be used for treating an entire row of teeth.

With the embodiment of FIG. 9, which in top plan appears identical with the illustration in FIG. 5B, the blade 5 of the unit 3 is of a substantially U-shaped configuration, conforming to a row of teeth, and this blade 5 is symmetrically situated with respect to the axis 2 of the shaft 4 of the unit 3 of FIG. 9. Thus with this embodiment the blade 5 can be situated between the upper and lower teeth in order to simultaneously expose both rows of teeth to the ultrasonic radiation.

Figure 10:
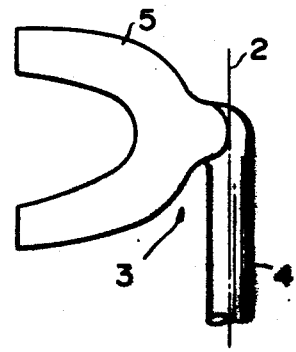
FIG. 10 shows a further embodiment of a shaft and blade according to which the blade can be used for treating an entire row of teeth.

The embodiment of FIG. 10 is substantially identical with that of FIG. 9, the only difference being that the U-shaped blade 5 extends laterally only to one side of the axis 2, with this blade 5 of FIG. 10 having a central axis situated midway between its legs extending perpendicularly with respect to the axis 2. This embodiment also can very conveniently be situated in the mouth between an entire row of upper teeth and an entire row of lower teeth for simultaneously treating both the upper and lower tooth rows. With these embodiments of FIGS. 9 and 10 the blade 5 will be held horizontally in the mouth between the upper and lower tooth rows, so that the lower end of faces of the upper teeth and the upper end faces of the lower teeth will be simultaneously treated, and the required treatment can be carried out in a relatively short time.

It is to be noted that while specific embodiments are described above and shown in the drawings it is also possible to vary these embodiments for example, by combining features of two or more of the above embodiments or appropriately modifying these embodiments so that different configurations can be effectively used for different purposes.

With all of the above embodiments, in view of the cost and moldability, a metal or plastic material is utilized as the material for the vibratory unit 3 which includes the shaft 4 and the blade 5. In general, it is preferred to use a metal having an appropriate rigidity and no toxic effect on the human body during the treatment while the unit is in the oral cavity. Thus, it is possible to use for the unit 3 material such as stainless steel, titanium, nickel, iron-aluminum alloy, or the like.

As has been indicated above, with all of the embodiments the vibratory unit 3 can be operatively connected with the vibrator means 1 in any suitable way according to which it is capable of transmitting the vibrations in a reliable manner. Instead of the above expedients of using keyed connections and set screws or the like, it is also possible to use suitable adhesives, or the shaft 4 can be directly welded or soldered to the vibrator means 1, or an extension of the latter can be forge welded so as to have the configuration of any of the above units 3, or even clamping by way of a suitable bolt can be utilized.

In order to provide a treatment with any of the above embodiments of the invention, the teeth to be treated are first placed in contact with a suitable tooth-decay retarding agent in the form of a suitable known powder, solution, or paste which includes an effective ingredient such as in fluoride, sodium fluoride, fluoroamine, or the like. This agent is placed, coated, or deposited on the surfaces of the teeth to be treated. Then the vibratory unit 3 of the invention is situated in the oral cavity close to the tooth-decay retarding agent to transmit ultrasonic waves to the tooth surfaces which are covered with this agent. Instead of directing the ultrasonic waves through a slight air space onto the surfaces of teeth which are coated in the above manner, it is also possible to propagate the waves through a medium such as liquid which naturally occurs in the human oral cavity or by way of water which is made to be present between the coated surfaces and the blade 5 in any suitable way such as by being fed from a suitable source to the space between the teeth and the blade 5 which is vibrated. When the ultrasonic waves have a relatively low frequency such as, for example, 19 KHz or 28 KHz, then the effective ingredient of the tooth-decay retarding agent can effectively permeate into the surface portions of the teeth through a relatively broad region, and a tight highly effective reinforcing layer can be formed throughout this relatively broad region during a single one-step treatment.

It is also possible to provide elongated channel-shaped trays for receiving the teeth to be treated with such trays having therein the treating agent which directly contacts the teeth, and these trays are shaped so that the blade 5 of any of the above embodiments can be situated in the tray together with the treating agent so that with such a construction also it is possible to treat the teeth in a highly effective manner, exposing the teeth to the ultrasonic radiation while the teeth are in the presence of the treating agent. It is also possible to engage the teeth with a flexible enclosure having therein a liquid such as water, and engaging the flexible enclosure with the plate 5 so as to transmit the ultrasonic waves through such a medium to the teeth. With a feature of this latter type, the flexible enclosure which contains the liquid can be porous so that the liquid in the flexible enclosure seeps through the wall thereof to engage the teeth, and this case the flexible enclosure can contain the tooth-decay retarding agent in a suitable liquid form, so that the ultrasonic waves are transmitted directly through the tooth-decay retarding agent itself which gradually seeps through the wall of such flexible enclosure into engagement with the teeth, providing in this way also a highly effective treatment. Thus, the apparatus of the invention can be used, with any of the above embodiments, not only for direct irradiation of ultrasonic waves to the tooth surfaces but also for indirect irradiation. Thus, as pointed out above, the surface of a tooth to be treated is initially coated with the tooth-decay retarding agent, and a soft flexible enclosure filled with an ultrasonic wave propagating medium such as water is placed so as to cover and engage the coated tooth, with the waves then being transmitted through such a medium.

Figure 11:
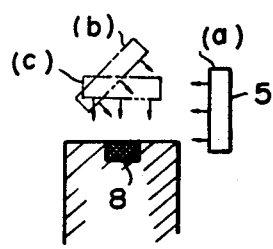
FIG. 11 is a schematic representation of different possible positions of a blade with respect to a tooth surface which is to be treated.
Figure 12:
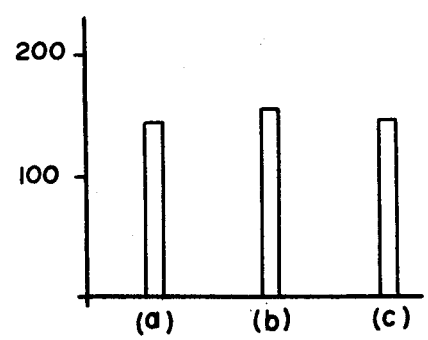
FIG. 12 is a graph illustrating the results achieved with the different blade positions of FIG. 11.

Experiments have proved that with the apparatus of the invention it is possible to reinforce tooth surfaces with a tooth-decay retarding agent effectively not only at surfaces of the teeth which are directed toward the surface of the blade 5 but also at other surfaces of the teeth which are oblique or even parallel to the direction of radiation. In this particular experiment, a spatula-like vibration source, having a width of 8 mm and a length of 2 cm, as shown in FIG. 4, was used for the particular vibratory unit 3, and the blade 5 of this unit was vibrated with an amplitude of up to $10\mu$ so as to radiate ultrasonic waves in a direction perpendicular to the surface of the blade 5. By utilizing such a unit 3, a sample was exposed to radiation with the ultrasonic waves having a frequency of 28 KHz while the surface to be treated was contacted by $SnF_2$ and the effect of the treatment was examined with the blade held in different positions with respect to the surface to be treated. Thus, referring to FIG. 11, for this experiment a sample 8 in the form of a portion of a tooth was embedded in a suitable carrier with the enamel surface of the sample 8 exposed in the manner indicated in FIG. 11. At position (a) the blade 5 was held so that the direction of radiation was parallel to the surface of the tooth, the angle of position (a) being 0°, in this case. At position (b) for the blade 5, as indicated in FIG. 11, the direction of radiation was at 45° with respect to the surface to be treated, while in the position (c) the blade 5 was oriented so that the direction of radiation was at 90°, directly toward the surface to be treated. Seven different tooth samples were treated in this way, at each of the above three positions of the blade, and average values were calculated with respect to Vickers hardness. The results of these tests are indicated in FIG. 12 from which it is apparent that the particular orientation of the blade 5 with respect to the surface to be treated is practically of no significance and the desired outstanding effect is achieved in each case.

What is claimed is:

1. For use in the treatment of teeth, a torsional ultrasonic vibrator comprising a shaft having a central axis, a blade fixed to said shaft and extending at least in part laterally therefrom, said blade being small enough to be situated in the mouth of an individual to be treated and large enough to extend along a plurality of teeth in the mouth of the individual to be treated, said shaft having opposed end regions and said blade being fixed to said shaft at one of said end regions thereof, said blade being flat and having a thickness which is substantially less than the diameter of said shaft, and said blade having a relatively narrow end region where said blade has a minimum width, said narrow end region of said blade being situated next to said shaft, and said blade having a configuration according to which said blade has a width substantially greater than the width of said narrow end region thereof at a location situated outwardly away from said shaft, so that said shaft can be situated at the exterior of the mouth of an individual to be treated directly next to the mouth while the narrow end region of said blade is situated directly next to said shaft at the entrance into the mouth of the individual to be treated and a portion of the blade which is wider than said narrow end region thereof is situated in the mouth for directing treatment to a plurality of teeth in the mouth, and vibrator means operatively connected with said shaft at the other of the opposed end regions thereof which is distant from said one end region to which said blade is fixed for angularly oscillating said shaft and said blade therewith about said axis at an ultrasonic frequency.

2. The combination of claim 1 and wherein said vibrator means has an elongated configuration and extends along said axis.

3. The combination of claim 1 and wherein said blade extends only to one side of said axis.

4. The combination of claim 1 and wherein said blade extends across said axis to both sides thereof and is substantially perpendicular thereto.

5. The combination of claim 4 and wherein beyond said narrow end region said blade has a substantially constant width in a direction extending across said axis, and said blade forming with said shaft a component of substantially T-shaped configuration.

6. The combination of claim 1 and wherein said blade has a thickness which gradually diminishes from said axis toward an outer tip of said blade which is most distant from said axis.

7. The combination of claim 1 and wherein said blade has a substantially triangular configuration and a relatively wide outer end region distant from said shaft and said blade gradually increasing in width, in the direction of said axis, from said shaft toward said outer end region of said blade.

8. The combination of claim 7 and wherein said blade is situated to one side only of said axis and terminates at its relatively wide outer end region in a substantially straight elongated edge which is parallel to said axis.

9. The combination of claim 1 and wherein said blade has a substantially U-shaped configuration for extending along an entire row of teeth.

10. The combination of claim 9 and wherein said blade is symmetrical with respect to said axis.

11. The combination of claim 9 and wherein said blade is situated on only one side of said axis.

* * * * *